(12) United States Patent
Kilmer et al.

(10) Patent No.: US 11,413,479 B2
(45) Date of Patent: Aug. 16, 2022

(54) METHOD OF CONTROLLING A POWERED AIR PURIFYING RESPIRATOR

(71) Applicant: 3M INNOVATIVE PROPERTIES COMPANY, St. Paul, MN (US)

(72) Inventors: Sean R. Kilmer, Lino Lakes, MN (US); Douglas D. Jensen, Woodbury, MN (US); Keith K. Mclaughlin, Eagan, MN (US); Andrew Murphy, Binchester Moor (GB)

(73) Assignee: 3M Innovative Properties Company, St. Paul, MN (US)

( * ) Notice: Subject to any disclaimer, the term of this patent is extended or adjusted under 35 U.S.C. 154(b) by 975 days.

(21) Appl. No.: 16/092,469

(22) PCT Filed: Apr. 5, 2017

(86) PCT No.: PCT/US2017/026143
§ 371 (c)(1),
(2) Date: Oct. 10, 2018

(87) PCT Pub. No.: WO2017/180391
PCT Pub. Date: Oct. 19, 2017

(65) Prior Publication Data
US 2019/0126077 A1 May 2, 2019

Related U.S. Application Data

(60) Provisional application No. 62/321,242, filed on Apr. 12, 2016.

(51) Int. Cl.
*A62B 18/00* (2006.01)
*A62B 18/04* (2006.01)
(Continued)

(52) U.S. Cl.
CPC .............. *A62B 18/006* (2013.01); *A62B 7/10* (2013.01); *A62B 18/045* (2013.01); *A62B 25/00* (2013.01);
(Continued)

(58) Field of Classification Search
CPC ....... A62B 18/006; A62B 7/10; A62B 18/045; A62B 25/00; A62B 9/006;
(Continued)

(56) References Cited

U.S. PATENT DOCUMENTS 4,899,740 A 2/1990 Napolitano
4,905,687 A * 3/1990 Ponkala ............... A62B 18/006
128/204.21

(Continued)

FOREIGN PATENT DOCUMENTS

EP 0518538 12/1992
GB 2032284 5/1980
(Continued)

OTHER PUBLICATIONS

Supplementary Search Report for Application EP17782858 dated Oct. 2, 2019.
(Continued)

*Primary Examiner* — Tu A Vo
(74) *Attorney, Agent, or Firm* — Steven A. Bern; Dena M. Ehrich

(57) ABSTRACT

Methods and systems for controlling a powered air purifying respirator blower system where volumetric airflow is stepped down into predetermined discrete ranges based on system loading and desired runtime.

3 Claims, 3 Drawing Sheets

(51) Int. Cl.
    *A62B 7/10*     (2006.01)
    *A62B 25/00*     (2006.01)
    *A62B 9/00*     (2006.01)
    *F04D 25/06*     (2006.01)
    *F04D 27/00*     (2006.01)
    *H02P 6/00*     (2016.01)
    *H02P 6/06*     (2006.01)

(52) U.S. Cl.
    CPC ........... *F04D 25/06* (2013.01); *F04D 27/004* (2013.01); *H02P 6/06* (2013.01); *A62B 9/006* (2013.01)

(58) Field of Classification Search
    CPC .............. A61M 16/0066; A61M 16/06; A61M 16/0051; A61M 2205/3317; A61M 2205/3334; A61M 2205/3341; A61M 2205/3365; A61M 2205/7545; A61M 2205/8212; F04D 25/06; F04D 27/004; H02P 6/06
    See application file for complete search history.

(56) References Cited

U.S. PATENT DOCUMENTS

| | | | |
|---|---|---|---|
| 5,950,621 | A | 9/1999 | Klockseth |
| 7,244,106 | B2 | 7/2007 | Kallman |
| 7,699,053 | B1 * | 4/2010 | Johnson ............... A62B 18/006 128/204.26 |
| 2002/0155860 | A1 | 10/2002 | Tordera |
| 2005/0071909 | A1 | 4/2005 | Diaz |
| 2005/0103343 | A1 * | 5/2005 | Gosweiler ........... A62B 18/006 128/205.12 |
| 2005/0133031 | A1 * | 6/2005 | Han .................. A61M 16/0808 128/204.17 |
| 2007/0240719 | A1 * | 10/2007 | Duarte ................... A62B 29/00 128/205.27 |
| 2008/0127979 | A1 | 6/2008 | Becker |
| 2009/0266361 | A1 | 10/2009 | Bilger |
| 2009/0314295 | A1 | 12/2009 | Hatmaker |
| 2010/0108066 | A1 | 5/2010 | Martin |
| 2010/0108067 | A1 | 5/2010 | Walker |
| 2011/0146682 | A1 * | 6/2011 | Patil ....................... A62B 18/08 128/204.21 |
| 2012/0017906 | A1 | 1/2012 | Hansmann |
| 2012/0051904 | A1 | 3/2012 | Hagen |
| 2012/0138051 | A1 * | 6/2012 | Curran ................. A62B 18/006 128/201.25 |
| 2012/0157794 | A1 | 6/2012 | Goodwin |
| 2012/0260918 | A1 | 10/2012 | Sayers |
| 2013/0087150 | A1 | 4/2013 | Palacharla |
| 2013/0104900 | A1 | 5/2013 | Tobias |
| 2013/0118487 | A1 | 5/2013 | Huh |
| 2014/0001376 | A1 | 1/2014 | Liu |
| 2014/0014102 | A1 | 1/2014 | Bowman |
| 2014/0311490 | A1 * | 10/2014 | Volmer .................. A62B 18/02 128/204.21 |
| 2015/0000651 | A1 * | 1/2015 | Palacharla ............. A62B 9/006 128/202.22 |

FOREIGN PATENT DOCUMENTS

| | | | |
|---|---|---|---|
| WO | WO 2009-067583 | 5/2009 | |
| WO | WO 2013-109242 | 7/2013 | |
| WO | WO 2015-175777 | 11/2015 | |
| WO | WO-2015187986 A1 * | 12/2015 | ............ A62B 18/02 |
| WO | WO 2017-180583 | 10/2017 | |

OTHER PUBLICATIONS

International Search report for PCT International Application No. PCT/US2017/026143 dated Jul. 6, 2017, 3 pages.

* cited by examiner

METHOD OF CONTROLLING A POWERED AIR PURIFYING RESPIRATOR

CROSS REFERENCE TO RELATED APPLICATIONS

This application is a national stage filing under 35 U.S.C. 371 of PCT/US2017/026143, filed Apr. 5, 2017, which claims the benefit of U.S. Provisional Application No. 62/321,242, filed Apr. 12, 2016, the disclosure of which is incorporated by reference in its/their entirety herein.

FIELD

The present invention relates to a blower system, and method of controlling a blower system, for use in a powered air purifying respirator (PAPR).

BACKGROUND

When working in areas where there is known to be, or there is a risk of there being, dusts, fumes or gases that are potentially hazardous or harmful to health, it is usual for the worker to use a respirator. A common type of respirator used in such circumstances is a powered air purifying respirator (PAPR). A PAPR has a blower system comprising a fan powered by an electric motor for delivering a forced flow of air to the respirator user. A turbo unit is a housing that typically contains the blower system, and is adapted to connect a filter to the blower system. Air is drawn through the filter by the blower system and passed from the turbo unit through a breathing tube to a headpiece, for example, a helmet or headtop, thus providing filtered air to the user's breathing zone (the area around their nose and mouth). A blower system for a PAPR may also include an electronic control unit to regulate the power driving the fan. Typically, a single power supply, for example a battery, provides power for both the fan and the electronic control unit.

The electronic control unit can be used, for example, to control the power to the electric motor with the aim of maintaining a substantially uniform volumetric airflow from the blower. The term "volumetric air flow" indicates the volume of air provided to a user at any one time as opposed to the mass of air provided to a user any one time. Sufficient airflow is required by the user to ensure that the designated level of respiratory protection is maintained. However, too high an airflow can cause discomfort and excessive cooling to the user's head inside the headpiece. Too low an airflow can cause ingress of contaminants into the user's breathing zone. The electronic control unit may also be used to trigger alarms to the user, for example, to alert the user if the airflow falls below a designated level, or to alert the user that the filters may be blocked with dust and need to be replaced. It has previously been proposed to control the power to the fan motor of a PAPR blower system in dependence on a combination of motor voltage, motor current and motor speed. Examples of blower control systems of that type are described in US 2008/0127979 (Becker et al.) and U.S. Pat. No. 7,244,106 (Kallman et al.).

US 2008/0127979 describes an electronic control system using a pulse width modulation (PWM) ratio as a control variable to generate a specific motor speed and a respective airflow. The PWM ratio is read from a calibration curve stored in the electronic control system.

U.S. Pat. No. 7,244,106 describes a control unit that detects the power consumption of the motor and the speed of the fan and compares this with a characteristic curve, stored in a memory, for the motor for a given airflow from the fan. In the event of a deviation from this characteristic curve, the control unit regulates a change in the voltage supplied to the motor to maintain a constant airflow.

A predetermined volumetric airflow of filtered air is usually intended to be delivered to the user of a PAPR to give a certain level of protection from the ingress of particles or gases into their breathing zone. Currently available systems often provide a volumetric airflow that is much higher than is actually needed, rather than risk a situation where too little air is provided. A higher airflow usually means that the battery life between charges is reduced or that larger batteries are required, as more power is consumed to provide the higher airflow. Filter life is also reduced by providing a higher airflow as excess contaminated air is moved through the filters leading to unnecessary filtering and premature clogging or saturation of the filters. As filters are consumable and require replacement many times over the lifetime of the PAPR, this can lead to higher running costs. A further problem is that in many PAPRs a low airflow alarm is required, alerting the user to the fact that the airflow has fallen below a predetermined level. Where an inaccurate airflow measuring or control system is used, the alarm level is often set at an artificially high level to ensure that the user is always safe. This in turn can lead to filters being changed too frequently or the user leaving the workplace unnecessarily. Hence it can be seen that more accurate control of the airflow at a particular volumetric airflow can lead to improved battery lives between charges or the use of smaller and lighter batteries, improved filter life and reduction of premature low airflow alarms. All of these factors can also lead to the improved productivity of the user.

US 2012/0138051 (Curran) describes a method of controlling a powered air purifying respirator blower to deliver a substantially uniform volumetric airflow to a user by taking into consideration one or more ambient air characteristics when controlling the blower.

Conventional PAPRS, having flow control, stay at a constant flow rate throughout the filter loading or battery range. This type of flow control enables the use of multiple control airflow rates in a PAPR. Users can decide to run at high airflow or low airflow. A typical user wants to run at higher airflow rate for as long as possible to aid in cooling. If a user is in a high filter loading environment, however, the high airflow rate will result in shorter filter life and shorter battery life, resulting in shorter system run times. One way this is dealt with is to provide PAPRs with large filters and large batteries to enable standard run times of typically 250 minutes).

It is desirable therefore to use a method of controlling a PAPR that minimizes such issues while maintaining or improving the overall functionality of the PAPR. It is also desirable to provide a method that ensures users will obtain at least 250 minutes of use from a fully charged battery. It is further desirable to provide a method that ensures users will obtain at least 250 minutes of use from a new filter.

SUMMARY

The present invention aims to further address these problems by providing a method that monitors filter usage and automatically adjusts airflow rate to optimize filter usage, particularly in harsh or high particulate environments.

In one aspect, the present invention provides a method of controlling a powered air purifying respirator blower system to deliver a substantially uniform volumetric airflow to a user, the system comprising a fan powered by a variable speed electric motor, the motor is controlled by an electronic control unit for delivering a forced flow of air through at least one filter to a user, comprising the steps of: (a) monitoring system loading; and (b) decreasing a speed of the electric motor when system loading reaches a predetermined value.

In some embodiments, the presently disclosed method further comprises (c) detecting a speed of the electric motor and establishing an electrical characteristic applied by the electronic control unit to the electric motor. In some embodiments, the presently disclosed method further comprises step (d) decreasing the speed of the electric motor to a speed lower than the speed established in step (b) by providing the electrical characteristic to the electric motor as determined in step (c).

In some embodiments, wherein the substantially uniform volumetric airflow from the fan is varied based on the speed of the electric motor. In some embodiments, the substantially uniform volumetric airflow from the fan is variable and chosen from any one of a number of pre-selected airflow values. In some embodiments, the electrical characteristic is voltage provided from a power supply.

In another aspect, the present disclosure provides an air purifying respirator blower system, comprising a fan powered by an electric motor, and an electronic control unit operable to adjust an electrical characteristic of the electric motor in accordance with a predetermined correlation between the speed of the fan and the applied motor electrical characteristic for a selected substantially uniform volumetric airflow from the fan; wherein the system further comprises one or more sensors adapted to be in communication with the electronic control unit and arranged to determine system loading, the electronic control unit being operable in response to the system loading, to adjust an electrical characteristic applied to the electric motor to account for a change in system loading and decrease the selected substantially uniform volumetric airflow from the fan.

In some embodiments, the presently disclosed air purifying respirator blower system also comprises a housing wherein the housing further includes at least one filter positioned in the airflow path of the fan. In some embodiments, the presently disclosed air purifying respirator blower system also comprises a housing wherein the housing further includes a power supply for the motor.

In some embodiments, the electric motor is a three-phase square-wave brushless direct-current motor. In some embodiments, the aforementioned blower system is in fluid communication with either a respirator headpiece or a full-face respirator in order to provide a powered air purifying respirator.

The above summary of the present disclosure is not intended to describe each embodiment of the present invention. The details of one or more embodiments of the invention are also set forth in the description below. Other features, objects, and advantages of the invention will be apparent from the description and from the claims.

BRIEF DESCRIPTION OF THE DRAWINGS

By way of example only, embodiments of the invention will now described below with reference to the accompanying drawings, in which.

DETAILED DESCRIPTION

Figure 1:
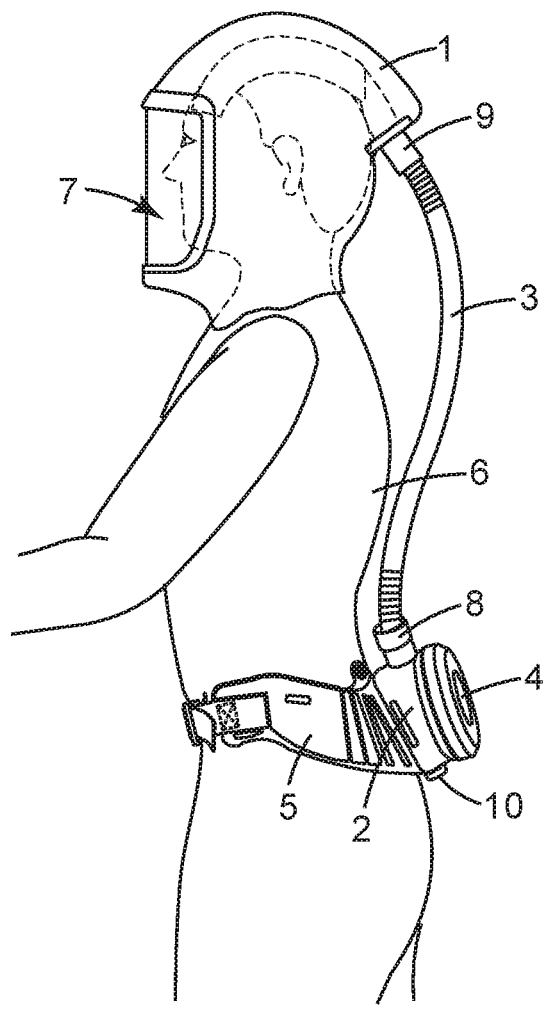
FIG. 1 is a diagrammatical illustration of a powered air purifying respirator.

Before any embodiments of the invention are explained in detail, it is to be understood that the invention is not limited in its application to the details of construction and the arrangement of components set forth in the following description. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Any numerical range recited herein includes all values from the lower value to the upper value. For example, if a percentage is stated as 1% to 50%, it is intended that values such as 2% to 40%, 10% to 30%, or 1% to 3%, etc., are expressly enumerated. These are only examples of what is specifically intended, and all possible combinations of numerical values between and including the lowest value and the highest value enumerated are to be considered to be expressly stated in this application.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface"

with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

The term "altering" as used herein means automatically increasing or decreasing the air flow rate of the PAPR.

The term "system loading" as used herein means an amount of particulate loading in a filter used in the system. For example, in some embodiments, the system loading is a measurement of the revolutions per minute ("rpm") detected for a fan used to draw air into and/or circulate air in the system. In some embodiments, the system loading is a measurement of the rpm of a motor used to power such a fan. In some embodiments, the system loading is a measurement of an electrical characteristic, such as voltage, used to power the motor used in the system. In some embodiments, the system loading is a measurement of pressure drop across a filter used in the system. In some embodiments, the system loading is a combination of any two or all of the aforementioned options.

Each of the embodiments described below employ a turbo as shown in FIG. 1. FIG. 1 is a diagrammatical illustration of a powered air purifying respirator. The PAPR comprises a headpiece 1, a turbo unit 2, a breathing tube 3, a filter 4 and a belt 5. Headpiece 1 is worn on the user's 6 head. It at least partially encloses the user's 6 head to form a breathing zone 7, that is, the area around their nose and mouth, so that the filtered air is directed to this breathing zone 7. Turbo unit 2 may be attached to a belt 5 to enable it to be secured about the user's 6 torso. Turbo unit 2 houses a blower system (not shown), which draws the air through the PAPR system using a fan (also not shown). Turbo unit 2 supplies air to headpiece 1 through breathing tube 3, which is connected between outlet 8 of turbo unit 2 and inlet 9 of headpiece 1. Turbo unit 2 is fitted with a filter 4, which can be either inside turbo unit 2 or attached to turbo unit 2 as shown in FIG. 1 such that filter 4 is in an airflow path, preferably disposed upstream of a fan opening of the blower. The purpose of providing filter 4 is to remove particles and/or gases and/or vapours from the ambient air before the air is delivered to user 6. A battery pack 10, which is fitted to turbo unit 2 provides power to an electronic control unit 23 and to a motor 22 (both shown in FIG. 2 as discussed below).

Headpiece 1 may have a variety of configurations. Although a hood is illustrated in FIG. 1, headpiece 1 could be a helmet, a mask, or a full suit, provided it covers at least the orinasal area of the user's face, to direct air to user's 6 breathing zone 7. Full face respirators or half face mask respirators may be used as headpieces in conjunction with the embodiment of the present invention. Alternative ways of supporting turbo unit 2 on a user's 6 body or otherwise are also within the scope of the present disclosure. For example, a backpack-type support may be provided for turbo unit 2.

Generally when using a helmet or hood in a PAPR, a higher constant airflow is desired, than when a mask is used. Where user 6 may change between helmets and masks, or where the turbo unit 2 is shared between multiple users, it is desirable to have a range of substantially uniform volumetric airflows. The range of substantially uniform volumetric airflows may be continuously variable between a first airflow rate and a second airflow rate, or may be a series of discrete steps between the first and second airflow rates. For example, a system may be set to a first predetermined airflow value for use with a helmet or hood to a second, lower predetermined airflow value for use with a mask.

A PAPR may also be designed with smaller and lighter batteries, and smaller and lighter or lower profile filters. Turbo unit 2 may be fitted with more than one filter 4 in the airflow path, to remove particles and/or gases and vapours from the ambient air before the air is delivered to user 6. Filter(s) 4 may be inside turbo unit 2 or fitted to the outside of turbo unit 2. Battery 10, may be attached to turbo unit 2 as illustrated in FIG. 1 or may be remote from turbo unit 2 and connected by a suitable cable.

The following illustrates how the blower system in accordance with some embodiments of the present disclosure may operate. In the following examples, the structural components of the PAPR may be assumed to be as described above with reference to FIGS. 1 and 2.

Figure 2:
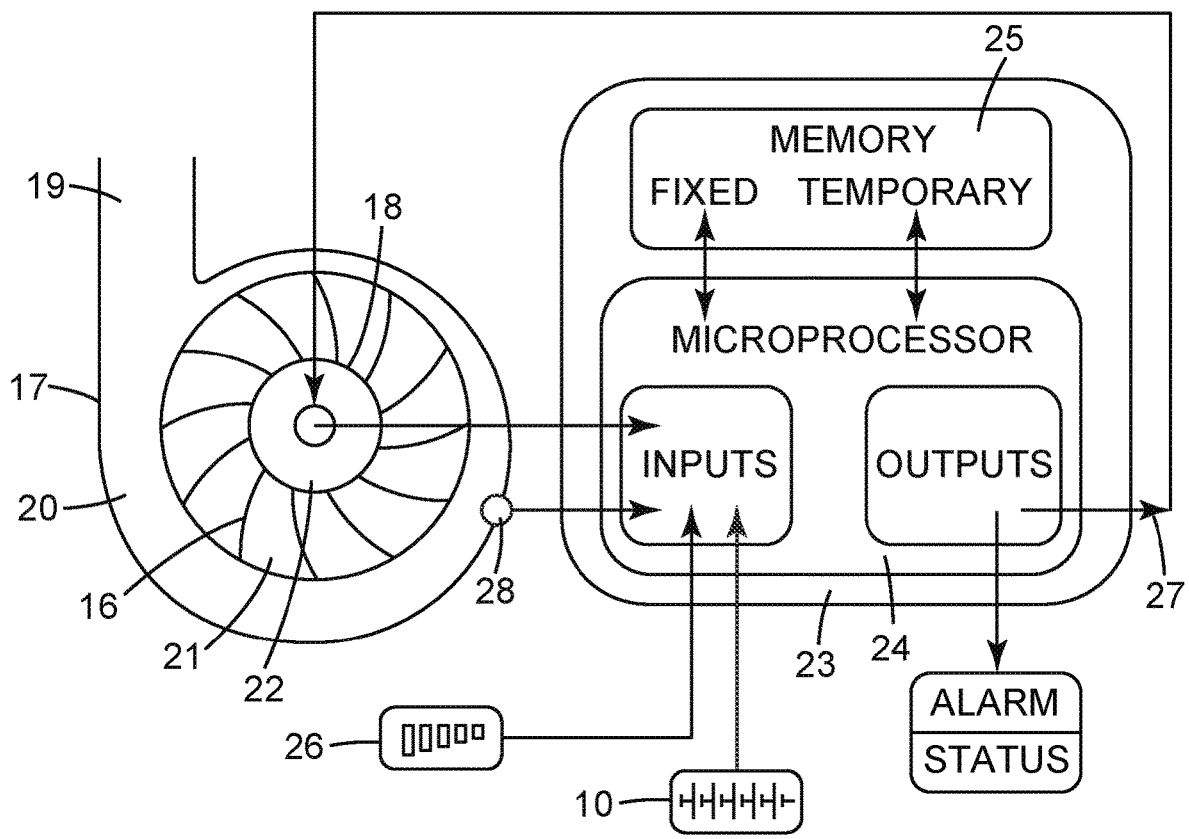
FIG. 2 shows a block diagram of a blower system according to a first embodiment of the present disclosure.

FIG. 2 shows a block diagram of a blower system according to a first embodiment of the present disclosure. The blower system is housed within turbo unit 2 as, for example, illustrated in FIG. 1. In some embodiments, a blower 20 includes a housing 17 having an inlet 18 and an outlet 19. Blower 20 includes a fan 21, having a plurality of blades 16, driven by a motor 22. Blower 20 is controlled by electronic control unit 23, which regulates the power provided from a power supply (such as battery 10 as depicted in FIG. 1) to motor 22. In some embodiments, the power supply is a battery, an electric cord that can be plugged into a power outlet, a solar cell, and the like. In some embodiments, a preferred power supply is a battery containing gas gauging circuitry, such as batteries that use standard System Management Bus ("SMBus") communications to provide an input 26 to microprocessor device 24. Exemplary commercially available SMBus gas gauges are available under the trade designation "TI BQ20Z90" from Texas Instruments Inc. Dallas, Tex. USA. In some embodiments, the power supplied from power supply to motor 22 is an electrical characteristic, such as for example, voltage.

It is desirable that a substantially uniform volumetric airflow be supplied to a user's 6 breathing zone 7, such that when user 6 inhales, sufficient filtered air is available for user 6 to breathe easily and normally, and no potentially contaminated ambient air is inhaled. A substantially uniform volumetric airflow is preferably, but not limited to, an airflow rate where the deviation from the desired or predetermined airflow is in the range −15 to +15 liters per minute.

In order to achieve a substantially uniform volumetric airflow at a particular volumetric airflow rate, either the airflow must be known or a correlation between various operating parameters and the required airflow must be known. It is possible to monitor the volumetric airflow by using a discrete airflow sensor. However, in the present disclosure, it has been appreciated that various operating parameters of fan 21 and motor 22 including fan or motor speed, motor voltage, motor current and motor power can be used to determine the volumetric airflow as described below.

With further reference to FIG. 2, the blower system comprises electronic control unit 23 that functions to maintain a substantially uniform, preferably constant, volumetric airflow to headpiece 1. Electronic control unit 23 comprises: a microprocessor device 24, such as a single chip microcontroller, for computing information; a memory device 25, such as flash RAM, for storing information; inputs to microcontroller include data from sensors such as motor current sensors and fan speed sensors 28, battery gas gauge 26 and voltage provided by battery 10; and an output controller 27, such as a pulse width modulation controller chip, for providing power to motor 22 and any alarm or status indicators, such as buzzers or light emitting diodes, that may be included in the PAPR. Memory device 25 of electronic control unit 23 has two parts: a fixed memory and a temporary memory. The fixed memory is populated with data, for example, at the time of manufacture, comprising the algorithms and programs for enabling microprocessor 24 to carry out its calculations and procedures, and calibration information from the factory calibration procedure. The temporary memory is used for storing data and information such as sensor readings and fan operating parameter data collected during start-up and running of turbo unit 2. If desired, this data maybe erased when turbo unit 2 is powered down.

In some embodiments, a three-phase square-wave, brushless, direct current motor 22 may be used to drive fan 21 of blower 20. The equations below, EQ. 1, EQ. 2 and EQ. 3 are well known and show the relationships between the main parameters of such a motor.

$$T = k_T I \quad \text{(Eq. 1)}$$

$$E = k_E \frac{2\pi}{60} n \quad \text{(Eq. 2)}$$

$$V_s = E + R_m I \quad \text{(Eq. 3)}$$

$T$  Air gap torque (*mNm*)
$k_T$  Torque constant (*mNm*/A)
$I$  Motor current (A)
$E$  Back *EMF* (V)
$k_E$  Back *EMF* constant (*Vs*/rad)
$n$  Speed (*rpm*)
$V_s$  Applied motor voltage (V)
$R_m$  Winding resistance (Ω)

Motor 22 used in the embodiments described above is a three-phase square-wave brushless direct-current motor. Alternatively, a segmented commutator brushed direct current motor may be used. Equations EQ. 1, EQ. 2 and EQ. 3 are known to be true for both the brushed and brushless types of motors. Consequently, most types of direct current motors known within the respirator industry could be used in presently disclosed blower 20. Other non-direct current types of motors that are known for PAPR applications may also be used. Alternative motor control methods, such as pulse width modulation are also envisaged as being within the scope of the present invention.

As explained above, blower 20 comprises a fan 21, which is used to move air through filter(s) 4 and deliver it to user 6. Fan 21 illustrated in the drawings is of the type often known as a centrifugal or radial fan, meaning that the air enters the fan in the direction of the fan axis and exits in a radial direction to the fan.

Still referring to FIG. 2, fan speed is measured by means of a sensor 28 fitted to blower 20 that measures the number of revolutions of fan 21 in a given time. A suitable type of sensor for measuring the fan speed would be a Hall effect device, although other types of sensor could be used. The fan speed 28 information is received by microprocessor device 24 of electronic control unit 23. Output to controller 27 can be voltage applied to electric motor 22.

In some embodiments, air should be delivered to user 6 at a predetermined substantially uniform volumetric airflow. In certain circumstances, however, user 6 may need to be able to adjust the airflow to a different level. For example if user 6 is working particularly hard and breathing more deeply or at a faster rate than usual, they may desire to increase the airflow. To enable this, in some embodiments, electronic control unit 23 is provided with a discrete range of two, three or more different, pre-set airflow values, for example, preferably 185 actual liters per minute, more preferably 205 actual liters per minute and most preferably 225 actual liters per minute for a hood or helmet, and preferably 135 actual liters per minute, more preferably 150 actual liters per minute and most preferably 170 actual liters per minute for a mask. In some embodiments, electronic control unit 23 is provided with an algorithm that allows continuous monitoring and varying of the airflow rate at various airflow values. However, electronic control unit 23 is usually set such that it is not possible for user 6 to inadvertently reduce the airflow below a level where the minimum protection is given.

Figure 3:
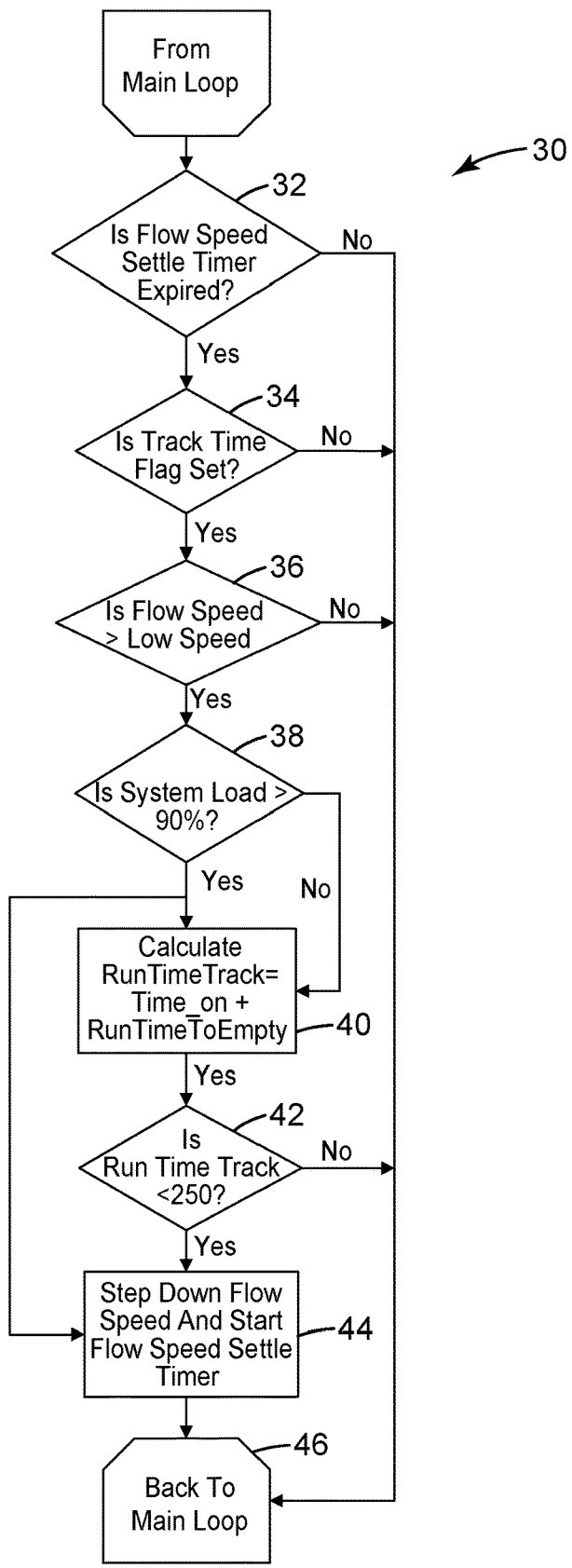
FIG. 3 is a flow chart illustrating an exemplary step down algorithm useful for controlling the presently disclosed powered air purifying respirator.

Referring now to FIG. 3, a method 30 is shown that automatically adjusts airflow rate to reduce power drawn from the battery when battery life is diminished. Method 30 is run within previously disclosed electronic microprocessor device 23 and used to control motor 22, which is in communication with fan 21 and battery pack 10. Method 30 provides a step 32 for determining whether air flow rate is stabilized. For example, a useful method may use a timer and a predetermined time during which an original manufacturer's defined air flow speed is expected to stabilize or settle timer is expired. For example, a useful method may ask whether an air flow speed settle timer has expired, after which the next step in the method is pursued. Referring again to FIG. 3, if air flow rate is not stabilized, presently disclosed method 30 will return to a main loop 46 step, bypassing the rest of the method.

If air flow rate is stabilized, method 30 provides a second step 34 for determining whether a track time flag is set. This step ensures that the system is tracking system run time. If not, presently disclosed method 30 will return to a main loop 46 step.

If a track time flag is set, method 30 provides a third step 36 for determining whether the presently running air flow speed is greater than the lowest speed possible for the system being run. If the presently running air flow speed is not greater than the lowest speed possible for the system being run, presently disclosed method 30 will return to a main loop 46 step.

If a presently running air flow speed is greater than the lowest speed possible for the system being run, method 30 provides a fourth step 38 for determining if system loading is greater than a determined value. In some embodiments, the determined value of the system loading is a filter load set to a predetermined value, such as a filter load of greater than 90 percent of the operational range per air flow rate. In some embodiments, usage data about filter load can be stored and accessed by microprocessor 24 module, such as in memory device 25. Usage data may include the length of time filter(s) 4 has been worn by the user. Usage data may also include the length of time filter(s) 4 has been in active use. Usage data can include a variety of types of information related to user's 6 wearing and use of filter(s) 4, the environment in which filter(4) have been used and stored, and other information relating to its use. Any of these values can be used, alone or in combination, to determine system loading value in step 38 of the presently disclosed method. For example, usage data can be used to calculate a running, real time filter load time remaining.

Referring again to FIG. 3, method 30 provides that, if system loading is not greater than a determined value as determined in step 38, method 30 provides a fifth step 40 of determining an estimated system run time (RunTimeTrack) by summing a battery run time remaining (RunTimetoEmpty) and a system run time (Time_On). If system loading is greater than a determined value as determined in step 38, in some embodiments, method 30 jumps to a subsequent step 44 of altering air flow speed, such as for example decreasing or stepping down air flow speed, and starting an air flow speed settle timer. In some embodiments, air flow speed settle timer is set to a certain time value, such as, for example 1 minute, 2 minutes, 3 minutes, 4 minutes, 5 minutes, 10 minutes, 15 minutes, and the like. In some embodiments, air flow speed settle timer is not set to a specific time value or this step is completely omitted, which would also obviate the need for step 32. In some embodiments, the air flow speed may be decreased to a predetermined values as defined above. This step may be repeated for which the decreases in air flow rate may be conducted in incremental, predetermined steps, which may be called "Stepped Down Flow Speed(s)". In some embodiments, there can be 1, 2, 3, 5 or more different incremental, predetermined steps for decreasing air flow rate. In some embodiments, there can be an unlimited number of different incremental, predetermined steps for decreasing air flow rate. In some embodiments, altering air flow speed may include increasing air flow speed. In some embodiments, altering air flow speed may include both decreasing and increasing air flow speed. For example, in some embodiments, air flow is monitored and controlled in real time according to method 30.

Referring again to FIG. 3, once estimated system run time (RunTimeTrack) is determined in step 40, method 30 provides step 42 in which estimated run time is compared to a desired run time. For example, if a desired run time is 250 minutes, step 42 determines whether the estimated system run time (RunTimeTrack) is less than 250 minutes. If estimated system run time (RunTimeTrack) is not less than 250 minutes method 30 returns to main loop 46. If estimated system run time (RunTimeTrack) is less than 250 minutes, method 30 advances to step 44, as previously disclosed, for altering air flow speed, such as for example decreasing or stepping down air flow speed, and starting an air flow speed settle timer. Once step 44 is complete, method 30 returns to main loop 46. In some embodiments, step 42 is optional.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," or "controller" as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

Various modifications and alterations of this invention will become apparent to those skilled in the art without departing from the scope and spirit of this invention.

What is claimed is:

1. A method of controlling a powered air purifying respirator blower system airflow to a user, comprising a fan powered by a variable speed electric motor, the motor controlled by an electronic control unit for delivering a forced flow of air through at least one filter to a user, comprising the steps of:
    (a) monitoring system loading;
    (b) decreasing a speed of the electric motor when system loading reaches a predetermined value;
    (c) detecting the speed of the electric motor after step (b) and using the detected speed to determine if an estimated system run time is lower than a desired system run time, and if the estimated system run time is lower than the desired system run time, establishing an electrical characteristic that could be applied by the electronic control unit to the electric motor that would bring the estimated system run time to be not less than the desired system run time; and
    (d) decreasing the speed of the electric motor to a speed lower than the speed established in step (b) by applying the electrical characteristic to the electric motor as determined in step (c).

2. The method of claim 1, wherein the airflow from the fan is variable and chosen from any one of a number of pre-selected discrete airflow values that each provides a different substantially uniform volumetric airflow.

3. The method of claim 1, wherein the electrical characteristic is voltage provided from a power supply.

* * * * *